United States Patent [19]

Bhansali

[11] Patent Number: 5,283,330
[45] Date of Patent: Feb. 1, 1994

[54] 1,2-BENZO-8-(D,L ALANYL)-3-PHENOXAZONE NITRATE

[76] Inventor: Kantilal G. Bhansali, 7622 Braesdale La., Houston, Tex. 77071

[21] Appl. No.: 944,170

[22] Filed: Sep. 11, 1992

[51] Int. Cl.⁵ ............................................. C07D 265/34
[52] U.S. Cl. ........................................ 544/99; 514/885
[58] Field of Search ............................ 544/99; 514/885

[56] References Cited

U.S. PATENT DOCUMENTS

| 3,580,947 | 5/1971 | Ikeda et al. | 544/99 |
| 3,655,601 | 4/1972 | Ottawa et al. | 544/99 |
| 4,611,056 | 9/1986 | Guindon et al. | 544/99 |

OTHER PUBLICATIONS

"The Chemical Estimation of Tyrosine and Tyramine"; Udenfriend et al, J. Biol Chem 1952, 196 pp. 227–233.

Primary Examiner—Marianne M. Cintins
Assistant Examiner—Catherine Scalzo
Attorney, Agent, or Firm—Kurt S. Myers

[57] ABSTRACT

The present invention is directed to the compound 1,2-benzo-8-(D,L alanyl)-3-phenoxazone nitrate and to the method for preparing this compound.

2 Claims, 3 Drawing Sheets

1,2-BENZO-8-(D,L ALANYL)-3-PHENOXAZONE NITRATE

FIELD OF THE INVENTION

The present invention is directed to 1,2-benzo-8-(D,L alanyl)-3-phenoxazone nitrate and a method for the preparation of the compound. More particularly, the present invention involves the preparation of 1,2-benzo-8-(D,L alanyl)-3-phenoxazone nitrate and its use as a potential cancer treating drug.

BACKGROUND OF THE INVENTION

The reaction of 1-nitroso-2-naphthol with tyramine and tyrosine in the presence of nitric acid has been reported by Udenfriend et al., J. Biol. Chem. 1952, 196, pp.227–233. Specifically, it is disclosed:

"TYROSINE DERIVATIVE—To 200 mg. of 1-nitroso-2-naphthol dissolved in 150 ml. of ethanol were added 80 mg. of L-tyrosine dissolved in 300 ml. of 1M nitric acid. The mixture was heated at 55° for 2 hours, cooled, and extracted four times with 500 ml. portions of ethylene dichloride to remove excess nitrosonaphthol. The nitrosonaphthol derivative was then extracted into 250 ml. of n-butanol, which was washed twice with equal volumes of water to remove dissolved acid. 1 liter of n-heptane was added to the n-butanol and the mixture was extracted with 200 ml. of water. Orange crystals appeared in the aqueous layer. These were collected on a sintered glass filter and washed with water. The moist crystals were readily soluble in water. The absorption spectrum was qualitatively the same as that of the isolated nitrosonaphthol tyramine derivative (FIG. 1). When dried in vacuo, the material was no longer easily soluble in water and displayed a changed absorption spectrum, indicating that a chemical change had occurred."

The reaction of 1-nitroso-2-naphthol with tyramine or tyrosine was used for quantitative analysis of either tyramine or tyrosine; however, as set forth by Udenfriend et al.: "The method does not distinguish between tyrosine or tyramine." A product was produced by the reaction, usually red to yellow, which related to the concentration of tyrosine or tyramine added, but the reaction product was not identified. The quantitative analysis of materials known or suspected to contain tyrosine or tyramine were reacted with 1-nitro-2-naphthol in the same manner as the controlled reaction and the color intensity measured by a spectrophotometer. The concentration of tyrosine or tyramine was determined by comparing the measured reading from the spectrophotometer to a calibrated chart having the color intensity for known concentrations.

SUMMARY OF THE INVENTION

The present invention is directed to the compound 1,2-benzo-8-(D,L alanyl)-3-phenoxazone nitrate and to the method for preparing this compound.

DESCRIPTION OF THE PREFERRED EMBODIMENT

Figure 1:
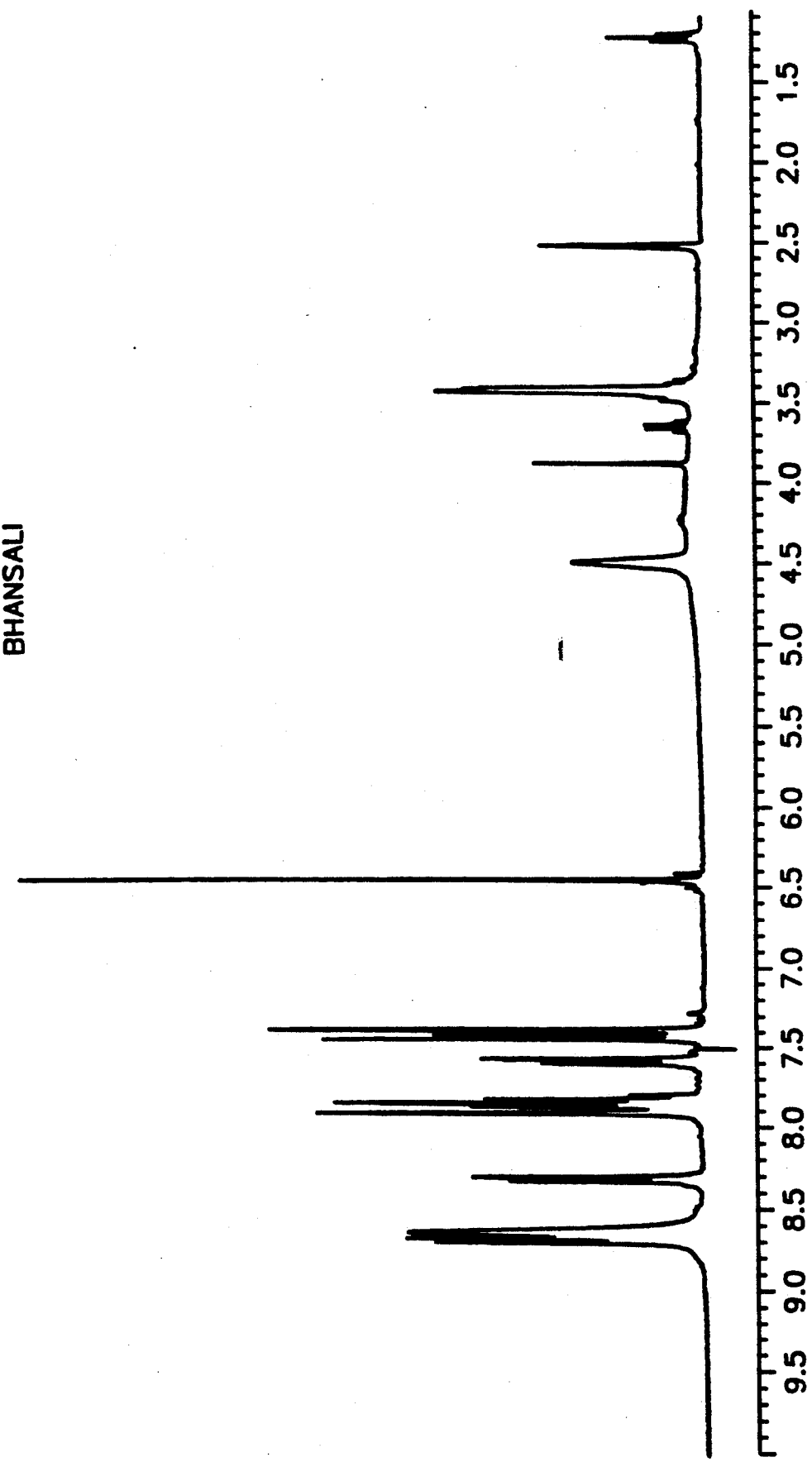
FIG. 1 is the $^1$H NMR spectrum of 1,2-Benzo-8-(alanyl)-3-phenoxazone nitrate in DMSO-d$_6$, at 292° C. (marked BHANSALI).

The reaction of 1-nitroso-2-naphthol with tyrosine and nitric acid is reported by Udenfriend et al. as follows: "To 200 mg. of 1-nitroso-2-naphthol dissolved in 150 ml. of ethanol were added 80 mg. of L-tyrosine dissolved in 300 ml. of 1 N nitric acid." This reported procedure will sometimes produce a product and sometimes hardly any crystals will appear, especially after the extractions with the n-butanol and n-heptane.

Surpisingly, when the procedure was changed and the following procedure followed, significant reaction occured and crystals appeared after extraction with dichloroethane only:

To a 500 ml. flask containing ethanol (150 ml.), D,L tyrosine (400 mg.) was added and mixed. To this mixture was added 1-nitroso-2-napththol (1.0 g.). Then, to this mixture was added in small increments 1.2N nitric acid (250 ml.). The mixture was heated at 60° C. for two hours, then cooled in an ice bath. The whole mixture was transfered into a separatory funnel and extracted three times with portions (60 ml.) of ethylene dichloride to remove excess nitroso-naphthol. Reddish orange crystals appeared from the alcohol-nitric acid solution at the bottom of the separatory funnel. The crystals were removed and filtered.

This procedure consistently produces a product where significant crystals are formed. These crystals were analyzed and found to have the following structure:

1,2-benzo-8-(D,L alanyl)-3-phenoxazone nitrate

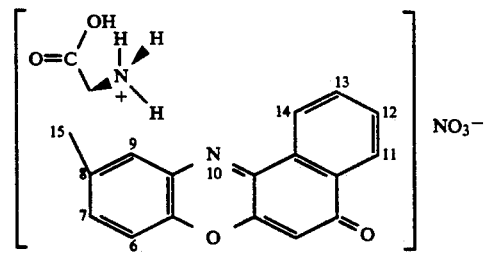

anal-calc. for $C_{19}H_{14}O_4N_2$; $HNO_3$; C, 57.43; H, 3.78; N, 10.58; found C, 57.41; H, 3.79; N, 10.65.

A comparison of the compound formed by the method of the present invention and crystals from the procedure set forth by Udenfriend were found to be different products. The crystals of the present invention are insoluble in water whereas the crystals from the Udenfriend procedure are reported as soluble in water.

Figure 2:
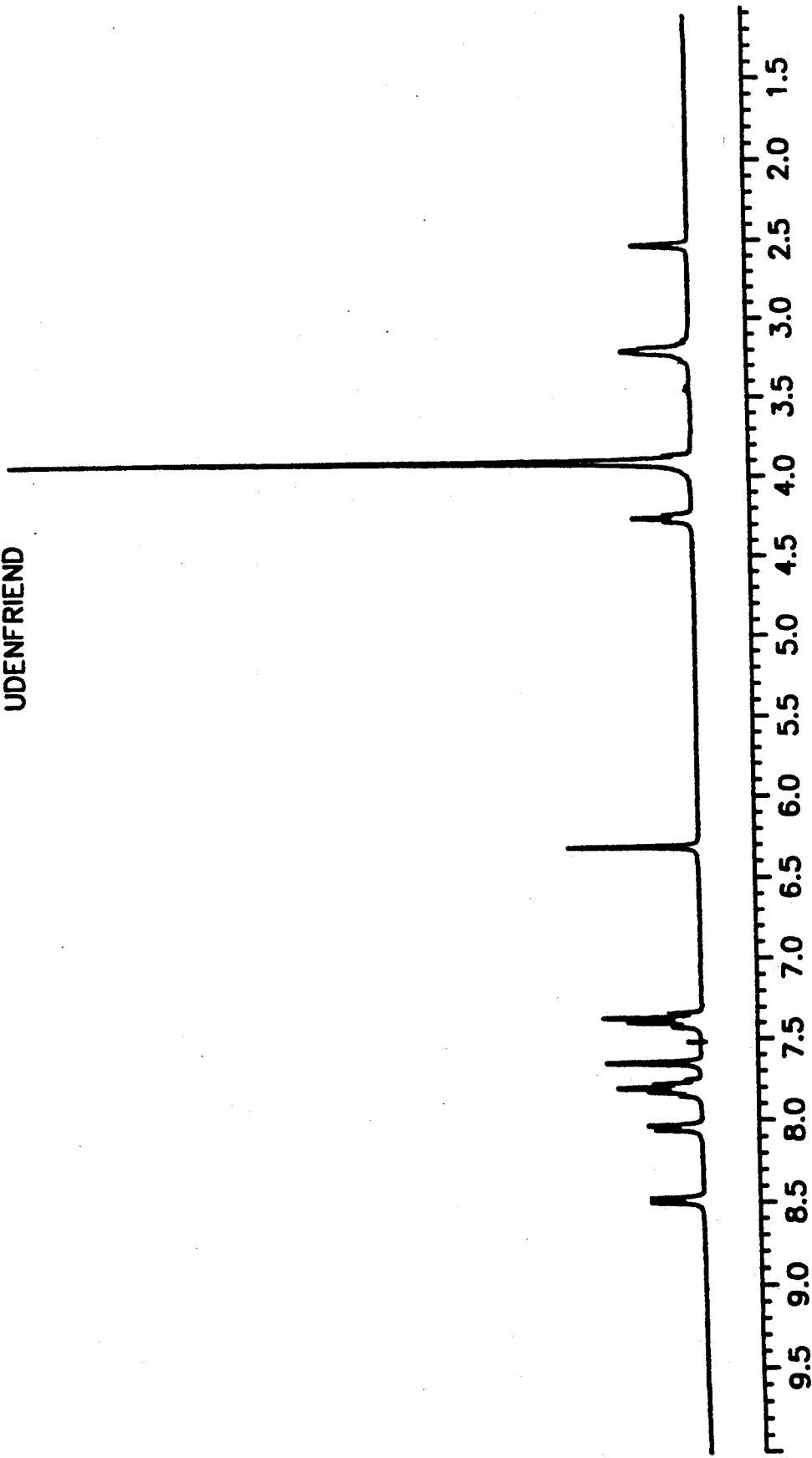
FIG. 2 is the $^1$H NMR spectrum of the material from the Underfriend reaction in DMSO-$_6$ at 292° C. (marked UDENFRIEND).
Figure 3:
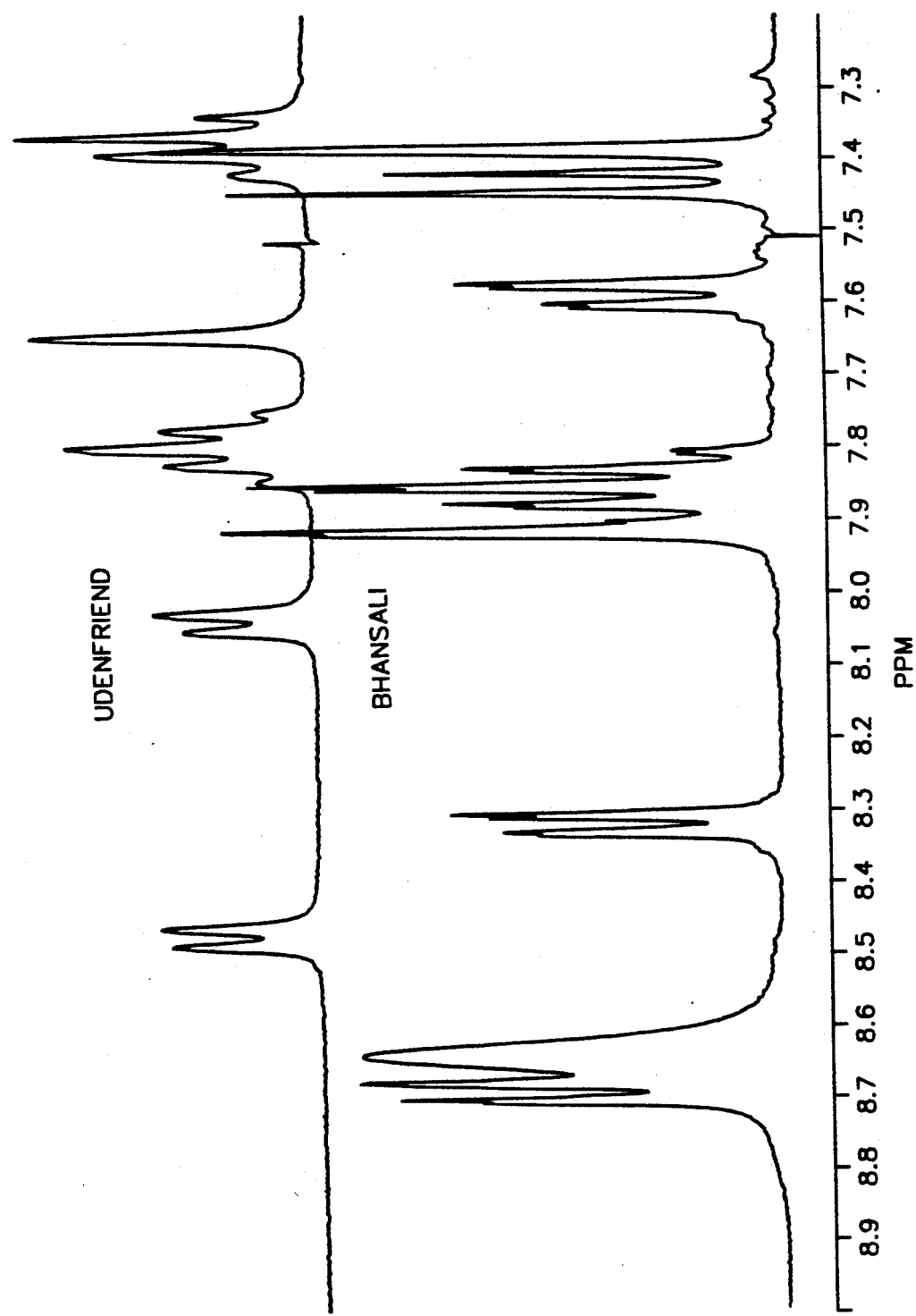
FIG. 3 is a comparison of the $^1$H NMR spectrum of 1,2-Benzo-8-(alanyl)-3-phenoxazone nitrate in DMSO-d$_6$ at 292° C. (marked BHANSALI) and the $^1$H NMR spectrum of the material from the Underfriend reaction in DMSO-d$_6$ at 292° C. (marked UDENFRIEND) both enlarged in the 7.3 to 8.9 PPM range.

A comparison of the crystals by $^1$H NMR spectroscopy showed that the products produced by each procedure are different and the crystals of the present invention were substantially pure without any solvent extractions with butanol or heptane which were part of the Udenfriend procedure. FIG. 1 shows the NMR spectrum of the crystals of the present invention and the strong peak between 6.4 and 6.5 PPM shows the 1,2-benzo-8-structure of the compound. The compound is a fully protonated salt which shows the $+NH_3$ protons at 8.65 PPM and -COOH proton at 7.40 PPM. FIG. 2 shows the NMR spectrum of the crystals of the Udenfriend procedure and the significant resonances are not present. FIG. 3 shows a comparison of the NMR spectrum of the two materials in the 7.2 to 9.0 PPM range where significant differences are most apparent.

The product of the present invention, 1,2-benzo-8-(D,L alanyl)-3-phenoxazone nitrate, is an analog of actinomycetin-D which intercalates with DNA. 1,2-benzo-8-(D,L alanyl)-3-phenoxazone nitrate may be less toxic than actinomycetin-D. It is known that the phenoxazones, like actinomycin-D, can intercalate between b-DNA base pairs in GC dinucletide regions. This interaction causes a widening of the gap between adjacent base-pairs by 2 angstrom or more. This re-orients the sugar-phosphate backbone and may cause unwinding of the base pairs further down the helix. The amino group in the side-chain can help further anchor the compound in the active site through hydrogen bonding with adjacent or nearest-neighbor base-pairs and/or electrostatic/ionic interactions with the sugar-phosphate backbone assisting in the further unwinding of the helix around the active site. Moreover, the compound might produce its effect by inhibiting enzyme(s) involved in cancer and AIDS.

In addition, the compound is being screened by the National Institute of Health, National Cancer Institute, as an active compound against cancer or AIDS and has been referred to the Biological Evaluation Committee by virtue of its activity and sub-panel disease selectivity. The compound has already shown in vitro sensitivity.

The compound of the present invention has been found to be an effective dye, especially a protein dye.

I claim:

1. 1,2-benzo-8-(D,L alanyl)-3-phenoxazone nitrate.

2. A method for producing 1,2-benzo-8-(D,L alanyl)-3-phenoxazone nitrate which comprises:
   mixing D,L tyrosine and 1-nitroso-2-naphthol in ethanol,
   to this mixture adding in increments nitric acid,
   heating the mixture for about two hours,
   cooling the whole mixture, and
   extracting the whole mixture with ethylene dichloride to remove excess nitroso-naphthol and recovering crystals from the resulting alcohol-nitric acid solution.

* * * * *

UNITED STATES PATENT AND TRADEMARK OFFICE
CERTIFICATE OF CORRECTION

PATENT NO. : 5,283,330

DATED : February 1, 1994

INVENTOR(S) : Kantilal G. Bhansali

It is certified that error appears in the above-identified patent and that said Letters Patent is hereby corrected as shown below:

Column 1, line 51 or 52, "1-nitro-2-naphthol" should read --1-nitroso-2-napththol--.

Column 2, line 2, between "DMSO-6" should read --DMSO-d--.

Column 2, lines 44 - 54, should be deleted and replace with the following drawing:

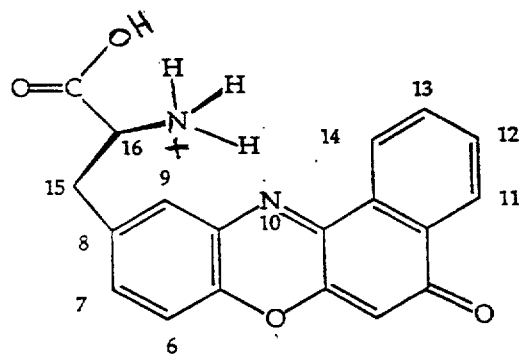

Signed and Sealed this

Sixteenth Day of August, 1994

Attest:

BRUCE LEHMAN

Attesting Officer   Commissioner of Patents and Trademarks